United States Patent [19]
Sloan et al.

[11] Patent Number: 5,472,966
[45] Date of Patent: Dec. 5, 1995

[54] ANTIDEPRESSANT HETEROARYLAMINOALKYL DERIVATIVES OF NAPHTHYL-MONAZINES

[75] Inventors: Charles P. Sloan, Wallingford; David W. Smith, Madison, both of Conn.

[73] Assignee: Bristol-Myers Squibb Company, New York, N.Y.

[21] Appl. No.: 412,625

[22] Filed: Mar. 29, 1995

[51] Int. Cl.$^6$ .................. A61K 31/495; A61K 31/505; A61K 31/445
[52] U.S. Cl. .................. 514/255; 514/269; 514/317; 514/318; 514/319; 544/333; 544/405; 546/184; 546/194; 546/205; 546/206; 546/236
[58] Field of Search .................. 546/184, 236, 546/205, 206, 194; 544/333, 405; 514/317, 319, 318, 269, 255

[56] References Cited

U.S. PATENT DOCUMENTS

| | | | |
|---|---|---|---|
| 5,166,156 | 11/1992 | Lavielle et al. | 514/255 |
| 5,250,544 | 10/1993 | Lavielle et al. | 546/205 |
| 5,292,711 | 3/1994 | Nishimura et al. | 503/209 |
| 5,292,761 | 3/1994 | Lavielle et al. | 514/357 |

FOREIGN PATENT DOCUMENTS

| | | |
|---|---|---|
| WO94/00441 | 1/1994 | WIPO. |
| WO94/02473 | 2/1994 | WIPO. |
| WO94/21619 | 9/1994 | WIPO. |

OTHER PUBLICATIONS

Glennon et al, "5-HT$_{1D}$ Serotonin Receptors: Results of a Structure–Affinity Investigation," *Drug Development Research*, 22:25–36 (1991).

*Primary Examiner*—C. Warren Ivy
*Assistant Examiner*—Amelia Owens
*Attorney, Agent, or Firm*—Richard P. Ryan

[57] ABSTRACT

Certain aminoalkyl derivatives of naphthyl-piperidines and tetrahydro-pyridines of Formula (I) are useful antidepressant agents.

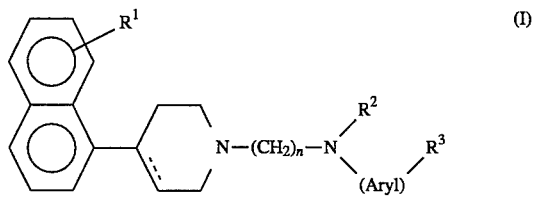

The symbol (Aryl) denotes phenyl, naphthyl, pyridinyl, pyrimidinyl and pyrazinyl ring systems with n being an integer of 2–4.

13 Claims, No Drawings

ANTIDEPRESSANT HETEROARYLAMINOALKYL DERIVATIVES OF NAPHTHYL-MONAZINES

BACKGROUND OF THE INVENTION

This invention generally pertains to heterocyclic carbon compounds having drug and bio-affecting properties and to their preparation and use. In particular, the invention is concerned with 4-(1-naphthyl)-piperidines and tetrahydropyridines with substituted aryl or hetarylaminoalkyl moieties attached at the N-1 position of the monazine. These compounds inhibit the reuptake of serotonin and potently bind at $5\text{-HT}_{1A}$, $5\text{-HT}_{1D}$ and $5\text{-HT}_2$ receptor sites. This pharmacology renders the compounds useful in treating depression. In addition, these compounds have reduced dopaminergic and α-adrenergic binding activities compared to diazine analogs such as piperazines.

Simple naphthylalkylamines and naphthylpiperazines have been reported to bind at $5\text{-HT}_{1D}$ receptor sites. (See: Glennon, et al., *Drug Development Research*, 22:25–36 (1991).)

Chenard, et al., WO 94 121619 disclosed a series of 1,7-disubstituted naphthalene derivatives (1) claimed to have, inter alia, antidepressant action. The central heterocyclic ring in (1) was

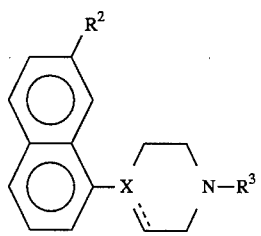

piperazine, dihydropyridine or piperidine while $R^3$ was hydrogen, alkyl, alkoxyalkyl, aryl or arylalkyl.

The most relevant art appears to be a series of U.S. patents to Lavielle, et al., that disclose and claim an extensive series of $5\text{-HT}_{1A}$ agonists (2) that are disclosed as being useful in treating a variety of disorders including depression.

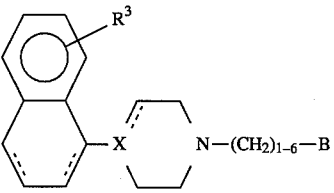

Lavielle, et al., discloses naphthylpiperidine (U.S. Pat. No. 5,250,544); naphthyl tetrahydropyridine (U.S. Pat. No. 5,292,711); and naphthyl piperazine (U.S. Pat. No. 5,166,156) analogs of (2), wherein B is an amido, sulfonamido, imido or phthalimido moiety. Also disclosed as synthetic intermediates are compounds wherein B is —CN and —NH₂.

Of less interest are the series of compounds of Tran, et al., WO 94 02473, wherein piperazine amides (3) were disclosed as having, inter alia, antidepressant properties.

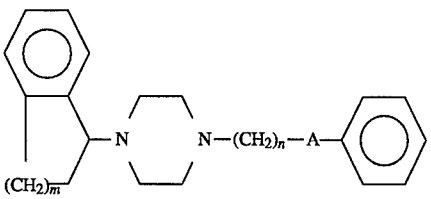

In (3), A is either —NHCO— or —CONH—.

Similarly, Perrone, et al., WO 94 00441 disclose piperazine derivatives (4) having antidepressant action among other biological activities.

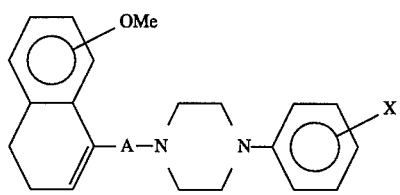

A in (4) is either —NH(CH₂)n— or —(CH₂)n—.

The foregoing references do not teach nor suggest the specific combination of structural variations leading to the novel secondary and tertiary aminoalkyl derivatives of 4-(1-naphthyl)-tetrahydropyridines and piperidines which not only possess specific 5-HT binding properties but also inhibit 5-HT reuptake. The added advantage of reduced dopaminergic and α-adrenergic activities make the instant compounds superior antidepressant agents.

SUMMARY AND DETAILED DESCRIPTION OF THE INVENTION

The present invention relates to novel secondary and tertiary aminoalkyl derivatives of 4-(1-naphthyl)-tetrahydropyridines and piperidines; their therapeutic use as specific serotonin receptor binders and serotonin reuptake inhibitors, particularly for treatment of depression with reduced side-effect potential; and their pharmaceutical compositions.

In a broad aspect, the present invention concerns compounds of Formula (I) having potent inhibition of serotonin reuptake and specific binding properties at certain 5-HT receptors. In addition, these compounds possess reduced dopaminergic and α-adrenergic activities, thereby imbuing them with a reduced potential for unwanted side-effects.

In Formula (I),

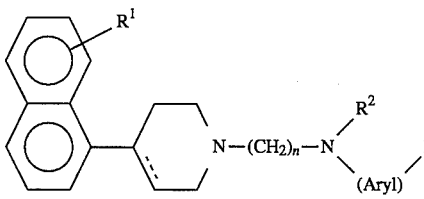

$R^1$ is hydrogen, lower alkyl, lower alkoxy, and halogen. The symbol n is an integer from 2 to 4. The solid and dotted lines denote either a single or a double covalent bond.

$R^2$ is hydrogen and lower alkyl and $R^3$ is hydrogen, lower alkyl, lower alkoxy, halogen and trifluoromethyl.

(Aryl) is selected from phenyl, naphthyl, pyridine, pyrimidine, and pyrazine.

Additionally, compounds of Formula (I) also encompass all pharmaceutically acceptable acid addition salts and/or solvates thereof. The present invention is also considered to include stereoisomers including optical isomers, e.g. mixtures of enantiomers as well as individual enantiomers which arise as a consequence of structural asymmetry in certain compounds of the instant series. Separation of the individual isomers is accomplished by application of various methods which are well known to practitioners in the art.

The term "lower" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2-methylpropyl. "Halogen" is fluorine, chlorine, bromine, or iodine.

The pharmaceutically acceptable acid addition salts of the invention are those in which the counter ion does not contribute significantly to the toxicity or pharmacological activity of the salt and, as such, they are the pharmacological equivalents of the bases of Formula (I). They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula (I) base with the selected acid, preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula (I) is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula (I) include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and others.

The compounds of Formula (I) and intermediate compounds can be prepared by adaptation of the synthetic processes shown in Schemes 1 and 2. In Scheme 1, two general reactions are depicted. The symbols "$R^1$, $R^2$, $R^3$, aryl, and n" are as defined supra. The monazine ring can be either a pipiradine or a tetrahydropyridine moiety. The symbol "X" denotes an organic synthetic leaving group such as a bromide, iodide, mesylate, tosylate and the like. Leaving groups (or nucleofuges) are well known to those skilled in synthetic organic chemistry. In reaction A, an amino intermediate of Formula (II) reacts with an electrophilic center in an aryl or hetaryl intermediate of Formula (III) to provide Formula (I) product. Reaction B shows the monazine intermediate of Formula (IV) undergoing nucleophilic displacement of X by compound (V) to also give a Formula (I) product.

Scheme 2 depicts the synthesis of several intermediate compounds, e.g. (II), (IV), (VI) and (X). In addition to the symbols previously described, other symbols in Scheme 2 are: "PG" meaning a protective group that insulates a nucleophilic moiety, e.g. an amino or hydroxy group; from reaction. Again, protective groups and their use are well known to synthetic organic chemists. The reagent "XY" denotes a leaving group X and its counter ion such as a proton or a halogen ion, e.g. XY could be $Br_2$, HBr, or tosyl bromide. Reaction A of Scheme 2 illustrates synthesis of the naphthylmonazine intermediates, either a tetrahydropyridine (XA) or piperidine (XB).

Reduction of the tetrahydropyridine ring to a piperidine can also be done further downstream in the synthesis of Formula (I) product such as at the compound (VI) or (II) stage.

Reaction sequence B shows the conversion of intermediate (X) to either the intermediate alcohol compound (VI) or the primary amine intermediate (IIA) via a Gabriel synthesis-type process.

Reaction sequence C illustrates the preparation of intermediates (IV) and (IIB) ($R^2$ is lower alkyl) from the alcohol compound (VI). These reactions and their application to ultimately arrive at the novel Formula (I) compound of this invention would be familiar to a practitioner skilled in organic chemical synthesis. Modifications of conditions and reagents to adapt these processes for preparation of specific Formula (I) compounds, including compounds embraced by this invention but not specifically disclosed, would be known to the skilled organic chemist.

Variations of the methods to produce the same compounds in somewhat different fashion will also be evident to one skilled in the art. To provide greater detail in description, representative synthetic examples are provided infra in the "Specific Embodiments" section.

The compounds of Formula (I) show potent inhibition of 5-HT re-uptake and can be envisioned as potential agents for disorders associated with dysfunction in serotonergic neurotransmission. Such disorders may include depression, anxiety, eating disorders, obesity, and drug abuse. In particular, the active compounds of the instant series are envisioned as specific agents for treating depression.

The compounds comprising the present invention inhibit the re-uptake of endogenous serotonin. Selective inhibitors of serotonin uptake are effective for the treatment of mental depression and have been reported to be useful for treating chronic pain (see: R. W. Fuller, Pharmacologic Modification of Serotonergic Function: Drugs for the Study and Treatment of Psychiatric and Other Disorders," *J. Clin. Psychiatry*, 47:4 (Suppl.) April 1986, pp. 4–8). Compounds of the present invention are also envisioned to be useful in the following disorders: obsessive-compulsive disorder, feeding disorders, anxiety disorders and panic disorders.

As a further indication of clinical antidepressant utility, the present series of compounds also demonstrate good $5-HT_{1A}$, $5-HT_{1D}$, and $5HT-_2$, binding activity. Side-effect potential in putative antidepressant agents can be ascertained by examination of the affinity of the agents for dopaminergic and adrenergic receptors. In the case of the instant compounds, these binding affinities are diminished.

Determination of endogenous monoaminergic re-uptake inhibition values for serotonin was accomplished using test methods described by P. Skolnick, et al., *Br. J. Pharmacology*, (1985), 86, pp. 637–644; with only minor modifications. In vitro $IC_{50}$ (nM) test values were determined for representative compounds of Formula I based on their inhibition of synaptosomal re-uptake of tritiated serotonin. Test data $IC_{50}$ values lower than 500 nM are considered to reflect activity as an inhibitor of serotonin re-uptake. Compounds with $IC_{50}$ values lower than 100 nM comprise preferred compounds and those with $IC_{50}$ value less than 10 nM are most preferred.

Another aspect of the instant invention provides a method for treating a mammal afflicted with depression or chronic pain which comprises administering systemically to said mammal a therapeutically effective amount of a compound of Formula I or a pharmaceutically acceptable acid addition salt thereof.

The administration and dosage regimen of compounds of Formula I is considered to be done in the same manner as for the reference compound fluoxetine, cf: Schatzberg, et al., *J. Clin. Psychopharmacology* 7/6 Suppl. (1987) pp. 4451–4495, and references therein. Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 10 mg/kg, preferably 0.1 to 1 mg/kg, when administered parenterally and from about 0.5 to about 10 mg/kg, preferably about 1 to 5 mg/kg, when administered orally. In some instances, a sufficient therapeutic effect can be obtained at lower doses while in others, larger doses will be required. Systemic administration refers to oral, rectal and parenteral (i.e. intramuscular, intravenous, transdermal and subcutaneous). Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$).

Analytical thin-layer chromatography (TLC) was performed on 0.25 mm EM silica gel 60 F-254 coated glass plates and preparative flash chromatography was performed on EM silica gel (36–62 µm). The solvent systems used are reported where appropriate. All reaction, extraction and chromatography solvents were reagent grade and used without further purification except tetrahydrofuran (THF) which was distilled from sodium/benzophenone ketyl. All non-aqueous reactions were carried out in flame-dried glassware under a nitrogen atmosphere.

A. SYNTHESIS OF INTERMEDIATES

Compounds of Formula (X)

Example 1—1,2,3,6-tetrahydro-4-(7-methoxy-1-naphthalenyl)pyridine

1-Iodo-7-methoxynaphthalene (1.0 g, 3.52 mmol) [CA#66240-21- 9] was dissolved in THF (50 mL) and cooled to −78 ° C. n-BuLi (2.1 mL, 4.57 mmol) was added quickly and after stirring at −78 ° C. for five min, N-BOC-4-piperidone (909 mg, 4.57 mmol) was added. The mixture was warmed to RT over one h then sat. ammonium chloride (1 mL) was added. The THF was removed in vacuo and the residue was extracted using CH$_2$Cl$_2$/brine. The CH$_2$Cl$_2$ was dried over Na$_2$SO$_4$ and evaporated to give the crude tertiary alcohol as a yellow oil which was then dissolved in dry CH$_2$Cl$_2$ (25 mL) and refluxed with trifluoroacetic acid (TFA) (5 mL) for 24 h. The mixture was evaporated in vacuo and the residue was extracted using CH$_2$Cl$_2$/dil. Na$_2$CO$_3$. The organic phase was dried over Na$_2$SO$_4$ and evaporated to give the crude product. Silica gel chromatography of the concentrate (95:5 to 1:0 EtOAc:hexane gradient) gave the title compound as a beige solid (490 mg, 58%). The purified material was dissolved in EtOAc and 2.0 eq. of fumaric acid in methanol was added. The solvents were removed, the solid was redissolved in a minimum amount of EtOH and the fumarate salt (257 mg, 35%) precipitated as a white powder upon addition of a small amount of EtOAc followed by cooling at 0° C., mp 190°–192° C.: IR (KBr) 1682, 1624, 1260, 1226, 824, 644 cm$^{-1}$; $^1$H NMR (DMSO-$d_6$) $\delta$ 2.59 (br s, 2H), 3.29 (t, j=5.87 Hz, 2H), 3.72 (br s, 2H), 3.80 (s, 3H), 5.70 (br s, 1H),7.03 (d, j=8.93 Hz, 1H), 7.13–7.23 (m, 3H), 7.60 (d, j=7.22 Hz, 1H), 7.65 (d, j=8.99 Hz, 1H): MS (DCI) m/e 240 (MH$^+$).

Anal. Calcd. for C$_{16}$H$_{17}$NO/1.0 C$_4$H$_4$O$_4$/0.2 H$_2$O: C, 66.92; H, 6.01; N, 3.90

Found: C, 66.71; H, 5.85; N, 3.87.

Example 2—4-(7-fluoro-1-naphthalenyl)-1,2,3,6-tetrahydropyridine

7-Fluoro-1-iodonaphthalene (1.73 g, 6.36 mmol) [CA#5079-77-5] was dissolved in THF (50 mL) and cooled to −78° C. n-BuLi (3.05 mL, 7.63 mmol) was added quickly and after stirring at −78 ° C. for five min, N-BOC- 4-piperidone (1.52 g, 7.63 mmol) was added. The mixture was warmed to RT over one hour then sat. ammonium chloride (1 mL) was added. The THF was removed in vacuo and the residue was extracted using CH$_2$Cl$_2$/brine. The CH$_2$Cl$_2$ was dried over Na₂SO₄ and evaporated to give the crude tertiary alcohol as a yellow oil which was then dissolved in anhydrous CH₂Cl₂ (50 mL) and refluxed with TFA (20 mL) for 24 h. The mixture was evaporated in vacuo and the residue was extracted using CH₂Cl₂ and dil. NaHCO₃. The CH₂Cl₂ was dried over MgSO₄, filtered, and concentrated to give the crude product. Silica gel chromatography (CH₂Cl₂ followed by 95:5:0.5 to 90:10:1 CH₂Cl₂:MeOH:NH₄OH gradient) gave the title compound as a beige solid (1.02 g, 71%). The purified material (0.5 g) was dissolved in EtOAc and 2.0 eq. of fumaric acid in methanol was added. The solvents were removed, the solid was redissolved in a minimum amount of EtOH and the fumarate salt (325 mg, 31%) precipitated as a white powder upon addition of a small amount of EtOAc followed by cooling at 0° C., mp 175°– 177° C.: IR (KBr) 1708, 1628, 1594, 1246, 1210, 982 cm⁻¹; ¹H NMR (DMSO-d₆) δ 2.60 (br s, 2H), 3.38 (t, j=5.95 Hz, 2H), 3.77 (br s, 2H), 5.75 (br s, 1H), 7.35 (d, j= 6.99 Hz, 1H), 7.41–7.50 (m, 2H), 7.80 (d, j= 11.4 Hz, 1H), 7.91 (d, j=8.12 Hz, 1H), 8.01–8.06 (m, 1H): MS (DCI) m/e 228 (MH⁺).

Anal. Calcd. for C₁₅H₁₄FN/2.0 C₄H₄O₄/0.7 H₂O: C, 58.52; H, 5.00; N, 2.97

Found: C, 58.18; H, 4.77; N, 3.06.

Example 3—4-(7-chloro-1-naphthalenyl)-1,2,3,6-tetrahydropyridine

1-Iodo-7-chloronaphthalene (1.0 g, 3.47 mmol) [CA#70109-79-4] was dissolved in THF (50 mL) and cooled to −78 ° C. n-BuLi (2.43 mL, 4.16 mmol) was added quickly and after stirring at −78° C. for five min, N-BOC- 4-piperidone (830 mg, 4.16 mmol) was added. The mixture was warmed to RT over 0.5 h then sat. ammonium chloride (1 mL) was added. The THF was removed in vacuo and the residue was extracted using CH₂Cl₂/brine. The CH₂Cl₂ was dried over MgSO₄, filtered, and evaporated to give the crude tertiary alcohol as a yellow oil which was then dissolved in dry CH₂Cl₂ (40 mL) and refluxed with TFA (15 mL) for 6 h. The mixture was evaporated in vacuo and the residue was extracted using CH₂Cl₂dil. Na₂CO₃. The CH₂Cl₂ was dried over Na₂SO₄ and evaporated to give the crude product. Silica gel chromatography (1:9 to 10:0 EtOAc:Hex gradient) gave a beige solid (330 mg, 39%). The free base (210 mg) was dissolved in EtOH, saturated with HCl(g), and the solvent removed. Recrystallization from EtOH/EtOAc gave the hydrochloride salt (130 mg, 53%) mp 216°–218 ° C.: IR (KBr) 2938, 2788, 2762, 2666, 2586, 822 cm⁻¹; ¹H NMR (DMSO-d₆) δ 2.64 (br s, 2H), 3.35 (br s, 2H), 3.42 (t, j=5.99 Hz, 2H), 3.81 (br s, 2H), 5.79 (br s, 1H), 7.40 (d, j=6.09 Hz, 1H), 7.54–7.59 (m, 2H), 7.95 (d, j= 8.21 Hz, 1H), 8.03 (d, j=8.79 Hz, 1H), 8.13 (d, j=2.00 Hz, 1H): MS (DCI) m/e 244 (MH⁺).

Anal. Calcd. for C₁₅H₁₄ClN /1.0 HCl/0.3 H₂O: C, 63.08; H, 5.51; N, 4.90.

Found: C, 63.05; H, 5.20; N, 4.92.

Compounds of Formula (VI)

Example 4—3,6-dihydro-4-(1-naphthalenyl)-1 (2H)-pyridinepropanol

A solution of 3-iodo-1-propanol (2.8 g, 15.06 mmol) and pulverized potassium carbonate (5.95 g, 43.03 mmol) in acetonitrile (150 mL) was added 3,6-dihydro-4-(1-naphthalenyl)-1(2H)-pyridine (3.0 g, 14.34 mmol) and the mixture refluxed for 18 h. The mixture was filtered and acetonitrile was removed in vacuo. The concentrate was dissolved in chloroform and extracted with aqueous 10% potassium carbonate. The aqueous phase was extracted three times with 250 mL portions of chloroform. The organic layers were combined and washed two times with 200 mL portions of saturated aqueous sodium chloride solution. The combined organic layers were dried over anhydrous magnesium sulfate, filtered, and concentrated to afford a solid. The crude solid was dissolved in minimal amounts of hot acetonitrile and left to cool to room temperature yielding 1.90 g (49.5%) of the title compound as a tan crystalline solid: ¹H NMR (CDCL₃): δ 1.83 (m, 2H), 2.57 (m, 2H), 2.81 (t, J=5.84 Hz, 2H), 2.87 (t, J=5.70 Hz, 2H), 3.29 (q, J=2.74 Hz, 2H), 3.89 (t, J=5.20 Hz, 2H), 5.42 (br s, 1H), 5.73 (m, 1H), 7.25 (d, J=1.58, 1H), 7.39–7.48 (m, 3H), 7.75 (d J=8.19, 1H), 7.83 (m, 1H), 7.96 (m, 1H)

Compounds of Formula (II)

Example 5  3,6-dihydro-N-methyl-4-(1-naphthalenyl)-1(2H)-pyridinepropanamine (IIB)

3,6-Dihydro-4-(1-naphthalenyl)-1(2H)-pyridinepropanol (Ex. 4: 1.20 g, 4.49 mmol) was dissolved in chloroform (50 mL) followed by the addition of triethylamine (0.94 mL, 6.73 mmol) and cooled to 0° C. Methanesulfonyl chloride (0.42 mL, 5.39 mmol) was added dropwise and the reaction was allowed to stir for thirty minutes while warming to room temperature. Solvent was then removed in vacuo yielding a crude solid (IV). This material was then dissolved in a solution of acetonitrile (60 mL) containing 40 wt. % aqueous methylamine (60 mL) and heated at reflux for three hours. The reaction was cooled to room temperature and concentrated in vacuo. The crude residue was diluted with chloroform (500 mL) and washed with aqueous 10% potassium carbonate (200 mL) followed by saturated aqueous sodium chloride (200 mL). The organic layer was dried over anhydrous magnesium sulfate, filtered, and concentrated yielding 1.20 g (98%) of the title compound as a viscous golden oil: ¹H NMR (CDCl₃): δ 1.80 (m, 2H), 2.05 (br s, 1H), 2.43 (s, 3H), 2.57 (m, 2H), 2.70 (t, J=Hz, 2H), 2.79 (t, J= Hz, 2H), 3.20 (m, 2H), 5.73 (m, 1H), 7.25 (d, J=1.58, 1H), 7.39–7.48 (m, 3H), 7.75 (d, J=8.19, 1H), 7.83 (m, 1H), 7.96 (m, 1H)

Example 6—3,6-dihydro-N-ethyl-4-(1-naphthalenyl)-1(2H)-pyridinepropanamine (IIB)

In a similar manner 3,6-dihydro-N-ethyl-4-(1-naphthalenyl)-1(2H)-pyridinepropanamine was prepared from 3,6-dihydro-4-(1-naphthalenyl)- 1(2H)-pyridinepropanol and ethylamine.

Example 7—3,6-dihydro-4-(1-naphthalenyl)-1(2H)-pyridinepropanamine (IIA)

A mixture of 1,2,5,6-tetrahydro-4-(1-naphthalenyl)pyridine (XA: 3.50 g, 16.75 mmol), N-(3-bromo)propylphthalimide (4.94 g, 18.42 mmol) and potassium carbonate (11.57 g, 83.mmol) in 330 mL of acetonitrile was heated to reflux for 16 h. The solvent was removed in vacuo and the residue was diluted with 200 mL of CH₂Cl₂ and 100 mL of 10% aqueous K₂CO₃. The aqueous layer was extracted serveral times with CH₂Cl₂. The combined organic layers were washed with brine, dried with MgSO₄, filtered, and evaporated in vacuo. Silica gel chromatography (1:4 to 1:1 EtOAc:hexane gradient) of the concentrate gave 5.24 g (13.23 mmol, 79%) of the desired phthalimide intermediate. To an EtOH (65 mL) solution of phthalimide intermediate was added hydrazine monohydrate (8.12 mL, 167.46 mmol) and sodium hydroxide (0.74 g, 18.43 mmol). The mixture was heated at reflux for 3 h. then cooled to ambient temperature and concentrated in vacuo. The residue was diluted with CH₂Cl₂ and 10% aqueous sodium carbonate. The organic phase was washed with brine, dried (Na₂SO₄), filtered, and evaporated in vacuo to give 3.70 g (13.90 mmol, 83%) of the title compound as an oil.

Example 8—4-(1-naphthalenyl)-piperidinepropanamine (IIA)

3,6-dihydro-4-(1-naphthalenyl)-1(2H)-pyridinepropanamine (1.0 g, 3.76 mmol), was dissolved in EtOH (80 mL) then water (10 mL) and 1N HCl (5 mL) were added. 10% Pd/C (500 mg) was added and the mixture was hydrogenated at 60 psi (RT) for 24 h. The catalyst was filtered over celite and the EtOH was removed in vacuo. The residue was dissolved in $CH_2Cl_2$, washed with dil. NaOH, and then with water. The $CH_2Cl_2$ layer was dried over $Na_2O_4$ and evaporated to give the crude product as a brown oil (0.92 g, 91%). The crude product was used without further purification: $^1H$ NMR ($CDCl_3$) δ 1.6–1.9 (m, 4H), 1.95– 2.10 (m, 2H), 2.15–2.3 (m, 2H), 2.4–2.5 (m, 2H), 2.7–2.8 (s, 4H), 3.14 (m, 2H), 3.33 (m, 1H), 7.05–7.15 (m, 1H), 7.2–7.35 (m, 3H), 7.72 (m, 1H), 7.85 (d, J=7.67 Hz, 1H), 8.10 (d, J=8.47 Hz, 1H).

Example 9—3,6-dihydro-4-(1-naphthalenyl)-1(2H)-pyridinebutanamine (IIA)

3,6-dihydro-4-(7-fluoro-1-naphthalenyl)-1(2H)-pyridine (1.00 g, 4.78 mmol) and N-(4-bromobutyl)phthalimide (1.48 g, 5.26 mmol) were dissolved in $CH_3CN$ (50 mL) and pulverized potassium carbonate (1.98 g) was added. The mixture was refluxed for 48 hours. Upon cooling to room temperature the crude mixture was filtered, diluted with chloroform (500 mL), and washed with 100 mL portions of agueous 10% potassium carbonate and saturated aqueous sodium chloride. The organic layer was dried over anhydrous magnesium sulfate, filtered, and concentrated in vacuo. The crude product was then dissolved in EtOH (75 mL) and refluxed with hydrazine hydrate (10 mL) for 6 h. NaOH (10.0M, 10 mL) was then added followed by $H_2O$ (20 mL) and the mixture stirred for an additional h. The solvents were removed in vacuo. The crude mixture was diluted with chloroform (500 mL) and washed with 75 mL portions of aqueous 10% potassium carbonate and saturated aqueous sodium chloride. The organic layer was dried over anhydrous magnesium sulfate, filtered, and concentrated to afford the title compound (1.06 g, 79%) which was used without purification: $^1H$ NMR ($CDCL_3$): δ 1.45 (m, 2H), 1.58 (m, 2H), 1.78 (br s, 2H), 2.50 (m, 2H), 2.78 (m, 2H), 3.18 (m, 1H), 5.71 (br s, 1H), 7.25 (d, J=1.58 Hz, 1H), 7.39–7.48 (m, 3H), 7.75 (d J=8.19 Hz, 1H), 7.83 (m, 1H), 7.96 (m, 1H).

Example 10—3,6-dihydro-4-(1-naphthalenyl)-1(2H)-pyridineethanamine (IIA)

In a similar manner 3,6-dihydro-4-(1-naphthalenyl)-1(2H)-pyridineethanamine was prepared from 1,2,3,6-tetrahydro-4-(1naphthalenyl)pyridine and N-(2-bromoethyl)phthalimide.

Example 11—3,6-dihydro-4-(7-methoxy-1-naphthalenyl)-1(2H)-pyridinepropanamine (IIA)

1,2,3,6-Tetrahydro-4-(7-methoxy-1-naphthalenyl)pyridine (XA: mol) was dissolved in $CH_3CN$ (50 mL) and micropulverized potassium carbonate (0.5 g) was added. The mixture was refluxed for 24 h, the solvent removed in vacuo, and the residue extracted using $CH_2Cl_2$/brine. The $CH_2Cl_2$ layer was dried over $Na_2SO_4$, filtered, and concentrated in vacuo to give the crude product as a brown oil. The concentrate was dissolved in EtOH (40 mL) and refluxed with hydrazine hydrate (5 mL) for one h. NaOH (50%, 1 mL) was added and the mixture refluxed for one h. The solvents were removed in vacuo and the residue extracted using $CH_2Cl_2$/brine. The $CH_2Cl_2$ layer was washed twice with water, dried over $Na_2SO_4$, filtered, and concentrated in vacuo. Silica gel chromatograpy of the concentrate (1:0 to 1:1 EtOAc:MeOH gradient) gave the free base (470 mg, 85%) as a brown oil. The free base (400 mg) was dissolved in EtOAc and treated with 2.0 eq. of fumaric acid in MeOH. Recrystallization from EtOH/EtOAc gave the title compound as a beige powder (310 mg, 43%), mp 176°–179° C.: IR (KBr) 1624, 1594, 1310, 1258, 1220, 1178$cm^{-1}$; $^1H$ NMR (DMSO-$d_6$) δ 1.80 (m, 2H), 2.57 (t, j=6.67 Hz, 2H), 2.74 (t, j=5.48 Hz, 2H), 2.88 (t, j=7.22 Hz, 2H), 3.17 (br s, 2H), 3.82 (s, 3H), 5.72 (br s, 1H), 7.15–7.31 (m, 4H), 7.73 (d, j=7.66 Hz, 1H), 7.83 (d, j=8.89 Hz, 1H); MS (DCI) m/e 297 ($MH^+$).

Anal. Calcd. for $C_{19}H_{24}N_2O/2.0\ C_4H_4O_4/0.1\ H_2O$: C, 60.77; H, 5.80; N, 5.13.

Found: C, 61.15; H, 6.12; N, 5.28.

Examples 12 and 13

3,6-dihydro-4-(7-chloro-1-naphthalenyl)- 1(2H)-pyridinepropanamine and 3,6-dihydro-4-(7-fluoro-1-naphthalenyl)- 1(2H)-pyridinepropanamine were prepared by reacting 4-(7-chloro-1-naphthalenyl- 1,2,3,6-tetrahydropyridine and 4-(7-fluoro-1-naphthalenyl)- 1,2,3,6-tetrahydropyridine, respectively, with N-(3bromophthalimide.

B. Synthesis of Products

The following examples illustrate product synthesis using reaction sequence A of Scheme 1 and employing Formula (IIB) intermediates.

Example 14—3,6-dihydro-N-(3-methoxy-2-pyridinyl)-N-methyl-4-(1-naphthalenyl)-1(2H)-pyridinepropanamine fumarate 3,6-Dihydro-N-methyl-4-(1-naphthalenyl)-1-(2H)-pyridinepropanamine (IIB: 330 mg, 1.18 mmol) was combined with 2-bromo- 3-methoxypyridine (266 mg, 1.41 mmol) and N,N-diisopropylethylamine (1.0 mL, 5.88 mmol) and heated in a bomb at 110° C. for 65 hours. Upon cooling to room temperature the crude mixture was diluted with chloroform (200 mL) and washed with 50 mL portions of aqueous 10% potassium carbonate and saturated aqueous sodium chloride. The organic layer was dried over anhydrous magnesium sulfate, filtered, and concentrated. Silica gel chromatograpy (97.5:2.5:0.25 $CH_2Cl_2$: MeOH:$NH_4OH$) of the concentrate gave the title compound (117 mg, 25.6%). The fumarate salt was made by dissolving the free base (79 mg, 0.20 mmol) along with fumaric acid (70 mg, 0.60 mmol) in a solution of hot EtOAc (10 mL) followed by the addition of minimal amounts of MeOH. Upon cooling to room temperature overnight the resultant crystals (48 mg, 38%) were collected by filtration and dried at 65° C. under vacuum (0.05 mm Hg) for 20 h, mp 120°–124° C.: M.S. (DCI); m/8388 ($MH^+$); I.R. (KBr); 1178, 1220, 1254, 1484, 1706; $^1H$ NMR ($D_2O$): δ 2.25 (m, 2H), 2.69 (br d, 1H), 2.86 (br m, 1H), 3.16 (s ,3H), 3.36 (t, J=8.43 Hz, 2H), 3.48 (m, 2H), 3.79 (t, J=7.22 Hz, 2H), 3.88 (m, 1H), 3.91 (s, 3H), 4.10 (br d, 1H), 5.78, (br s, 1H), 6.97 (t, J=7.95 Hz, 1H), 7.35 (d, J=7.01, 1H), 7.44–7.54 (m, 5H), 7.85–7.96 (m, 3H).

Anal. Calc'd. for $C_{25}H_{29}N_3O_1/2.0C_4H_4O_4$: C, 63.96; H, 6.02; N, 6.78.

Found: C, 63.81; H, 5.95; N, 6.97.

Example 15—3,6-dihydro-N-(3-ethoxy-2-pyridinyl)-N-methyl-4-(1- naphthalenyl)-1(2H)-pyridinepropanamine fumarate In a similar fashion 3,6-dihydro-N-(3-ethoxy-2-pyridinyl)-N-methyl- 4-(1-naphthalenyl)-1(2H)-pyridinepropanamine (134 mg, 30%) was synthesized from 2-bromo-3- ethoxypyridine and 3,6-dihydro-4-(1-naphthalenyl)-1(2H)-pyridinepropanol. The fumarate salt was made by dissolving the free base (134 mg, 0.33 mmol) along with fumaric acid (110 mg, 0.95 mmol) in a solution of hot EtOAc (10 mL) followed by the addition of minimal amounts of MeOH. Upon cooling to room temperature overnight the resultant crystals (136 mg, 77%) were collected by filtration and dried at 65 °C. under vacuum (0.05 mm Hg) for 20 h, mp 134°–135 °C.: M.S. (DCI); m/e 402 (MH$^+$); I.R. (KBr); 1210, 1390, 1490, 1580, 1700, 2500; $^1$H NMR (D$_2$O): δ 1.45 (t, J=6.96, 3H), 2.26 (m, 2H), 2.80 (br m, 2H), 3.11 (s, 3H), 3.37 (t, J=7.91 Hz, 2H), 3.57 (br s, 1H),3.72 (t,J=7.34Hz, 2H),3.91 (br m, 1H),4.18(q,J=6.99, 2H),4.75 (br s, 2H), 5.80, (br s, 1H), 7.00 (t, J=8.03, 1H), 7.40 (q, J=6.41, 2H), 7.51–7.60 (m, 4H), 7.90–7.98 (m, 3H).

Anal. Calc'd. for $C_{26}H_{31}N_3O_1/1.1C_4H_4O_4$: C, 68.99; H, 6.74; N, 7.94.

Found: C, 68.76; H, 6.48; N, 7.87.

Example 16—3,6-dihydro-N-methyl-N-(4-trifluoromethyl-2-pyridinyl)-4-( 1-naphthalenyl)-1(2H)-pyridinepropanamine fumarate In a similar fashion 3,6-dihydro-N-methyl-N-(4-trifluoromethyl-2-pyridinyl)- 4-(1-naphthalenyl)-1(2H)-pyridinepropanamine (314 mg, 47%) was synthesized from 2-chloro-4-trifluoromethylpyridine and 3,6-dihydro- 4-(1-naphthalenyl)-1(2H)-pyridinepropanol. The fumarate salt was made by dissolving the free base (314 mg, 0.74 mmol) along with fumaric acid (171 mg, 1.48 mmol) in a solution of hot EtOAc (10 mL) followed by the addition of minimal amounts of MeOH. Upon cooling to room temperature overnight the resultant crystals (250 mg, 63%) were collected by filtration and dried at 65° C. under vacuum (0.05 mm Hg) for 20 h, mp 174°–175° C.: M.S. (DCI); m/e 426 (MH$^+$); I.R. (KBr); 770, 1120, 1160, 1325, 1690, 2500; $^1$H NMR (D$_2$O): δ 2.18 (m, 2H), 2.74 (br m, 1H), 2.90 (br m, 1H), 3.10 (s ,3H), 3.32 (t, J=7.25 Hz, 2H), 3.47 (br m, 2H), 3.73 (br m, 3H), 4.03 (br m, 1H), 5.79 (br s, 1H), 6.91 (d, J=5.67, 1H), 7.05 (s, 1H), 7.37 (d, J=6.00, 1H), 7.48-7.56 (m, 3H), 7.88–7.97 (m, 3H), 8.15 (d, J=5.52, 1H).

Anal. Calc'd. for $C_{25}H_{26}N_3F_3/1.0C_4H_4O_4$: C, 64.32; H, 5.58; N, 7.76.

Found: C, 64.38; H, 5.32; N, 7.78.

Example 17—3,6-dihydro-N-methyl-N-(5-chloro-2-pyridinyl)-4-(1- naphthalenyl)-1(2H)-pyridinepropanamine fumarate In a similar fashion 3,6-dihydro-N-methyl-N-(5-chloro-2-pyridinyl)- 4-(1-naphthalenyl)-1(2H)-pyridinepropanamine (248 mg, 40%) was synthesized from 2,5-dichloropyridine and 3,6-dihydro-N-methyl-4-(1-naphthalenyl)-1-(2H)-pyridinepropanamine. The fumarate salt was made by dissolving the free base (248 mg, 0.63 mmol) along with fumaric (147 mg, 1.27 mmol) in a solution of hot EtOAc (10 mL) followed by the addition of minimal amounts of MeOH. Upon cooling to room temperature overnight the resultant crystals (214 mg, 67%) were collected by filtration and dried at 65° C. under vacuum (0.05 mm Hg) for 20 h, mp 180°–182° C.: M.S. (DCI); m/e 392 (MH$^+$); I.R. (KBr); 760, 800, 1160, 1300, 1500, 1710; $^1$H NMR (MeOD): δ 2.16 (m, 2H), 2.83 (br m, 2H), 3.07 (s, 3H), 3.30 (br m, 2H), 3.59 (t, J=5.97 Hz, 2H), 3.74 (t, J= 6.87 2H), 3.98 (br m, 2H), 5.80 (br s, 1H), 6.59 (m, 2H), 7.31 (d, J=7.04 Hz, 1H), 7.43–7.53 (m, 4H), 7.81–8.01 (m, 3H).

Anal. Calc'd. for $C_{24}H_{26}N_3Cl_1/1.0C_4H_4O_4$: C, 66.20; H, 5.95; N, 8.27.

Found: C, 65.81; H, 5.95; N, 8.27.

Example 18—3,6-dihydro-N-methyl-N-(6-trifluoromethyl-2-pyridinyl)-4-( 1-naphthalenyl)-1(2H)-pyridinepropanamine fumarate In a similar fashion 3,6-dihydro-N-methyl-N-(6-trifluoromethyl-2-pyridinyl)- 4-(1-naphthalenyl)-1(2H)-pyridinepropanamine (198 mg, 18%) was synthesized from 2-chloro-6-trifluoromethylpyridine and 3,6-dihydro-N-methyl- 4-(1-naphthalenyl)-1(2H)-pyridinepropanamine. The fumarate salt was made by dissolving the free base (198 mg, 0.47 mmol) along with fumaric (108 mg, 0.93 mmol) in a solution of hot EtOAc (10 mL) followed by the addition of minimal amounts of MeOH. Upon cooling to room temperature overnight the resultant crystals (44 mg, 17%) were collected by filtration and dried at 65° C. under vacuum (0.05 mm Hg) for 20 h, mp 144°–145° C.: M.S. (DCI); m/e 426 (MH$^+$); I.R. (KBr); 770, 1130, 1170, 1325, 1800–3600; $^1$H NMR (DMSO-d$_6$): δ 1.82 (m, 2H), 2.55 (t, J=6.92 Hz, 2H), 2.78 (t, J=5.51 Hz, 2H), 3.06 (s , 3H), 3.20 (m, 2H), 3.25 (br s, 2H), 3.62 (t, J=7.35 Hz, 3H), 5.69 (br s, 1H), 6.92 (d, J=8.49, 2H), 7.29 (d, J=7.03 Hz, 1H), 7.43–7.52 (m, 3H), 7.68 (t, J= 7.56, 1H), 7.82 (d, J=8.20 Hz, 1H), 7.89–7.97 (m, 2H).

Anal. Calc'd. for $C_{25}H_{26}N_3F_3/1.1C_4H_4O_4$: C, 63.84; H, 5.54; N, 7.60.

Found: C, 63.80; H, 5.53; N, 7.67.

Example 19—3,6.dihydro-N-methyl-N-(4-chloro-2-pyridinyl)-4-(1-naphthalenyl)- 1(2H)-pyridinepropanamine (A) and Example 20—3,6-dihydro-N-methyl-N-(2-chloro-4-pyridinyl)-4-(1-naphthalenyl)- 1(2H)-pyridinepropanamine fumarate (B)

3,6-Dihydro-N-methyl-4-(1-naphthalenyl)-1-(2H)-pyridinepropanamine (2.05 g, 7.30 mmol), 2,4-dichloropyridine (1.08 g, 7.30 mmol), and 4-methylmorpholine (10 mL) were heated in a Parr bomb at 140° C. for 72 h. Upon cooling to room temperature the crude mixture was diluted with chloroform (700 mL) and washed with 100 mL portions of aqueous 10% potassium carbonate and saturated aqueous sodium chloride. The organic layer was dried over anhydrous magnesium sulfate, filtered, and concentrated. Silica gel chromatography (50:50:1 toluene:EtOAc:NH$_4$OH) of the concentrate afforded 3,6-dihydro-N-methyl-N-(4-chloro-2-pyridinyl)-4-(1- naphthalenyl)-1(2H)-pyridinepropanamine (A) (244 mg) and 3,6-dihydro-N-methyl-N-( 2-chloro-4-pyridinyl)-4-(1-naphthalenyl)-1(2H)-pyridinepropanamine B) (190 mg). The fumarate salts were made by dissolving the free bases (232 mg (A), 0.59 mmol; 200 mg (B), 0.51 mmol) along with fumaric (137 mg, 1.18 mmol; 188 mg, 1.02 mmol respectively) in a solution of hot EtOAc (10 mL) followed by the addition of minimal amounts of MeOH. Upon cooling to room temperature overnight the resultant crystals (128 mg, 41% yield of A; 148 mg, 56% yield of B) were collected by filtration and dried at 65° C. under vacuum (0.05 mm Hg) for 20 h.

mp 151°–152° C. (A): M.S. (DCI); m/e 392 (MH$^+$); I.R. (KBr); 1200, 1400, 1590, 2100–3600; $^1$H NMR (DMSO-d6): δ 1.82 (m, 2H), 2.49 (m, 2H), 2.61 (t, J=7.32 Hz, 2H), 2.87 (t, J=5.46, 2H), 3.01 (s, 3H), 3.30 (br s, 2H), 3.59 (t, J=6.77 Hz, 2H), 5.70 (br s, 1H), 6.59 (m, 1H), 6.73 (d, J= 0.68 Hz, 1H), 7.30 (d, J=6.49 Hz, 1H), 7.44–7.51 (m, 3H), 7.87 (d, J= 8.11 Hz, 1H), 7.89–7.99 (m, 2H), 8.02 (d, J=5.35 Hz, 1H).

Anal. Calc'd. for $C_{24}H_{26}N_3Cl_1/1.1 C_4H_4O_4$: C, 65.65; H, 5.90; N, 8.09.

Found: C, 65.53; H, 5.64; N, 8.13.

mp 178°–179° C. (B): M.S. (DCI); m/e 392 (MH$^+$); I.R.

(KBr); 975, 1370, 1510, 1590, 1700, 2150–3600; $^1$H NMR (DMSO-d6): δ 1.80 (m, 2H), 2.49 (m, 2H), 2.57 (t, J=6.90 Hz, 2H), 2.83 (t, J=5.58, 2H), 2.97 (s, 3H), 3.25 (br s, 2H), 3.46 (t, J=6.91 Hz, 2H), 5.71 (br s, 1H), 6.66 (m, 2H), 7.30 (d, J=6.64 Hz, 1H), 7.44–7.52 (m, 3H), 7.83 (d, J=8.18 Hz, 1H), 7.87–7.99 (m, 3H).

Anal. Calc'd. for $C_{24}H_{26}N_3Cl_1/1.1C_4H_4O_4$: C, 65.65; H, 5.90; N, 8.09.

Found: C, 65.76; H, 5.72; N, 8.14.

Example 21—3,6-dihydro-N-(5-methoxy-4-pyrimidinyl)-N-methyl-4-(1-naphthalenyl)-1(2H)-pyridinepropanamine fumarate 3,6-dihydro-N-methyl-4-(1-naphthalenyl)-1-(2H)-pyridinepropanamine (365 mg, 1.30 mmol) was dissolved in a suspension of pulverized potassium carbonate (540 mg, 3.90 mmol) in acetonitrile (25 mL). 4-Chloro-5-methoxypyrimidine (251 mg, 1.95 mmol) was then added and the reaction was heated at reflux for 18 h. The mixture was filtered and acetonitrile was removed in vacuo. The residue was dissolved in chloroform and an aqueous 10% potassium carbonate solution and extracted three times with 100 mL portions of chloroform. The organic layers were combined and washed two times with 100 mL portions of saturated aqueous sodium chloride solution. The combined organic layers were dried over anhydrous magnesium sulfate, filtered, and concentrated in vacuo. Silica gel chromatography (100:0:0 to 98.5:1.5:0.15 $CH_2Cl_2$: $MeOH:NH_4OH$ gradient) of the concentrate yielded the free amine of title compound (0.57 g, 55%). The free amine was dissolved in a solution of hot EtOAc (10 mL) containing fumaric acid (164 mg, 1.41 mmol) and a minimal amount of MeOH to effect dissolution. Upon cooling to room temperature overnight the resultant crystals were collected by filtration and dried at 65° C. under 0.05 mm Hg for 24 h to yield the title compound (170 mg, 33%), mp 121°– 124° C.: M.S. (DCI), m/e 389 (MH$^+$); I.R. (KBr); 981, 1250, 1380, 1560, 1710; $^1$H NMR ($D_2O$): δ 2.24 (m, 2H), 2.68 (br d, 1H), 2.88 (br m, 1H), 3.35 (t, J=8.41 Hz, 2H), 3.42 (s, 2H), 3.46 (m, 2H), 3.73 (m, 1H), 3.85 (s, 3H), 3.95 (t, J=7.27 Hz, 2H), 4.10 (br d, 2H), 5.77, (br s, 1H), 7.35 (d, J= 7.22, 1H), 7.47–7.56 (m, 3H), 7.69 (s, 1H), 7.85–7.96 (m, 3H), 8.31 (s, 1H).

Anal. Calc'd. for $C_{24}H_{28}N_4O_1/2.9C_4H_4O_4/0.9H_2O_1$: C, 57.68; H, 5.63; N, 7.56.

Found: C, 57.39; H, 5.83; N, 7.90.

Example 22—3,6-dihydro-N-(5-methoxy-4-pyrimidinyl)-N-ethyl-4-(1-naphthalenyl)- 1(2H)-pyridinepropanamine fumarate In a similar manner 3,6-dihydro-N-(5-methoxy-4-pyrimidinyl)-N-ethyl- 4-(1-naphthalenyl)-1(2H)-pyridinepropanamine was prepared by reacting 3,6-dihydro-N-ethyl-4-(1-naphthalenyl)-1(2H)-pyridinepropanamine with 4-chloro-5-methoxypyrimidine: 59% yield, mp 127°–29° C.; m/e 403 (MH$^+$)

Anal. Calc'd. for $C_{25}H_{30}N_4O_1/2.9C_4H_4O_4/0.5H_2O_1$:C, 58.77; H, 5.74; N, 7.49.

Found: C, 58.46; H, 5.87; N, 7.83.

The following examples employ Formula (11A) intermediates.

Example 23—3,6-dihydro-4-(7-methoxy-1-naphthalenyl)-N-(5-methoxy- 4-pyrimidinyl)-1(2H)-pyridinepropanamine fumarate 3,6-Dihydro-4-(7-methoxy-1-naphthalenyl)-1(2H)-pyridinepropanamine (470 mg, 1.59 mmol) and 4-chloro-5-methoxy pyrimidine (275 mg, 1.91 mmol) were dissolved in acetonitrile (50 mL) and micropulverized potassium carbonate (1.0 g) was added. The mixture was refluxed for 24 h, the solvent removed in vacuo, and the residue extracted using $CH_2Cl_2$/brine. The $CH_2Cl_2$ layer was dried over $Na_2SO_4$, filtered, and concentrated in vacuo to give the crude product as a brown oil. Silica gel chromatography (95:5:0.5 $CH_2Cl_2$:$MeOH$:$NH_4OH$) of the concentrate gave the free amine (300 mg, 47%). The purified material was dissolved in EtOAc and 2.0 eq. of fumaric acid in MeOH was added. The solvents were removed, the solid was redissolved in a minimum amount of EtOH and the fumarate salt (375 mg, 66%) precipitated as a pale yellow powder upon addition of a small amount of EtOAc after cooling at 0° C., mp 105°–107 ° C.: IR (KBr) 1708, 1644, 1624, 1596, 1258, 1370 cm $^{-1}$; $^1$H NMR (DMSO-d6—d$_6$) δ 1.89 (m, 2H), 2.55 (br s, 2H), 2.78 (t, j=7.01 Hz, 2H), 3.00 (t, j=5.59 Hz, 2H), 3.42 (m, 4H), 3.80 (s, 3H), 3.82 (s, 3H), 5.74 (br s, 1H) 7.16–7.33 (m, 4H), 7.75 (d, j=5.69 Hz, 1H), 7.76 (s, 1H), 7.85 (d, j=8.95 Hz, 1H) 8.10 (s, 1H); MS (DCI) m/e 405 (MH$^+$).

Anal. Calcd. for $C_{24}H_{28}N_4O_2/2.7 C_4H_4O_4 0.5 C_2H_6O /0.3 C_4H_8O_2$: C, 57.91; H, 5.81; N, 7.30.

Found: C, 57.83; H, 6.00; N, 7.39.

In a similar manner 3,6-dihydro-4-(7-fluoro-1-naphthalenyl)-N-(5-methoxy- 4-pyrimidinyl)-1(2H)-pyridinepropanamine and 3,6-dihydro-4-( 7-chloro- 1 -naphthalenyl)-N-(5-methoxy-4-pyrimidinyl)-1(2H)-pyridinepropanamine were prepared by reacting 3,6-dihydro-4-(7-fluoro- 1-naphthalenyl)-1(2H)-pyridinepropanamine and 3,6-dihydro-4-(7-chloro-1-naphthalenyl)-1(2H)-pyridinepropanamine, respectively, with 4-chloro- 5-methoxypyrimidine.

Example 24—3,6-dihydro-4-(7-fluoro-1-naphthalenyl)-N-(5-methoxy-4-pyrimidinyl)-1(2H)-pyridinepropanamine fumarate mp 105°–107° C.: 52% yield; IR (KBr) 1706, 1646, 1596, 1372, 1268, 1248, 1210 cm$^{-1}$; $^1$H NMR (DMSO-d6-d$_6$) δ 1.92 (m, 2H), 2.56 (br s, 2H), 2.87 (t, j=6.97 Hz, 2H), 3.09 (t, j=5.58 Hz, 2H), 3.44 (m, 2H), 3.51 (br s, 2H), 3.81 (s, 3H), 5.73 (br s, 1H) 7.22 (t, j=5.69 Hz, 1H), 7.35–7.49 (m, 4H), 7.68 (d, j=8.87 Hz, 1H)7.77 (s, 1H), 7.88 (d, j=8.12 Hz, 1H) 8.00–8.05 (m, 2H), 8.10 (s, 1H); MS (DCI) m/e 393 (MH$^+$).

Anal. Calcd. for $C_{23}H_{25}N_4FO/2.6 C_4H_4O_4/0.6 C_2H_{60}$: C, 57.57; H, 5.45; N, 7.76.

Found: C, 57.30; H, 5.82; N, 7.39.

Example 25—3,6-dihydro-4-(7-chloro-1-naphthalenyl)-N-(5-methoxy-4-pyrimidinyl)-1(2H)-pyridinepropanamine fumarate mp 145°–150° C.: 48% yield; IR (KBr) 1708, 11642, 1600, 1370, 1274, 1174 cm $^{-1}$; $^1$H NMR (DMSO-$d_6$) δ 1.86 (m, 2H), 2.50 (br s, 2H), 2.71 (t, j=6.93 Hz, 2H), 2.92 (t, j=5.59 Hz, 2H), 3.35 (br s, 2H), 3.44 (m, 2H), 3.80 (s, 3H), 5.74 (br s, 1H) 7.22 (t, j=5.58 Hz, 1H), 7.38 (d, j=6.28 Hz, 1H), 7.49–7.55 (m, 2H), 7.76 (s, 1H), 7.89 (d, j=8.17 Hz, 1H) 7.95– 8.05 (m, 2H), 8.10 (s, 1H); MS (DCI) m/e 409 (MH$^+$).

Anal. Calcd. for $C_{23}H_{25}N_4ClO/2.6 C_4H_4O_4$: C, 56.45; H, 5.02; N, 7.88.

Found: C, 56.29; H, 5.06; N, 7.76.

Example 26—3.6-dihydro-4-(1-naphthalenyl)-N-(5-methoxy-4-pyrimidinyl)-1(2H)-pyridineethanamine fumarate In a similar manner 3,6-dihydro-4-(1-naphthalenyl)-N-(5-methoxy- 4-pyrimidinyl)-1(2H)-pyridineethanamine was prepared from 3,6-dihydro- 4-(1-naphthalenyl)-1(2H)-pyridineethanamine by reaction with 4-chloro-5-methoxypyrimidine:

mp 173°–175° C.: 73% yield; IR (KBr) 1702, 1644, 1588, 1560, 1538, 1260, 1186 cm$^{-1}$; $^1$H NMR (DMSO-d$_6$) δ 2.49 (m, 2H), 2.87 (t, j= 6.45 Hz, 2H), 2.98 (t, j=5.54 Hz, 2H), 3.41 (br q, 2H), 3.63 (q, j=6.2 Hz, 2H), 3.85 (s, 3H), 5.71 (br s, 1H), 7.04 (t, j=5.69 Hz, 1H), 7.30 (d, j=7.0 Hz, 1H), 7.44–7.53 (m, 3H), 7.80 (s, 1H), 7.82–7.98 (m, 4H),8.13 (s, 1H); MS (DCI) m/e 361 (MH$^+$).

Anal. Calcd. for $C_{22}H_{24}N_4O$ /2.0 $C_4H_4O_4$: C, 60.80; H, 5.44; N, 9.45.

Found: C, 60.80; H, 5.56; N, 9.42.

Example 27—3,6-dihydro-4-(1-naphthalenyl)-N-(5-methoxy-4-pyrimidinyl)- 1(2H)-pyridinepropanamine hydrochloride 3,6-Dihydro-4-(1-naphthalenyl)-1(2H)-pyridinepropanamine (0.97 g, 3.65 mmol), and 4-chloro-5-methoxypyrimidine (0.58 g, 4.0 mmol) were dissolved in acetonitrile (50 mL) and micropulverized potassium carbonate (1.0 g) was added. The mixture was refluxed for 24 h. The solvent was removed in vacuo and the residue extracted using CH$_2$Cl$_2$/ brine. The CH$_2$Cl$_2$ layer was washed with water, dried over MgSO$_4$, filtered, and concentrated in vacuo. Silica gel chromatography (100:0:0 to 90:10:1 CH$_2$Cl$_2$: MeOH:NH$_4$OH gradient) of the concentrate gave the free base (396 mg, 30%). The purified material was dissolved in EtOAc and HCl gas was bubbled through until no more precipitate formed. The EtOAc was removed, the solid was redissolved in a minimum amount of EtOH and pure HCl salt (132 mg, 26%) precipitated as a pale yellow powder upon addition of a small amount of EtOAc followed by slow cooling at RT, mp 137°–140° C.: IR (KBr) 2930, 2592, 1642, 1606, 1564, 1274 cm$^{-1}$; $^1$H NMR (DMSO-d$_6$) δ 2.18 (m, 2H), 3.07 (br d, 2H), 3.29 (br t, 2H), 3.73 (br m, 4H), 3.68 (t, j=5.93 Hz, 2H), 3.98 (s, 3H), 5.76 (br s, 1H), 7.02 (d, j=7.05 Hz, 1H), 7.50–7.58 (m, 2H), 7.90 (d, j=8.5 Hz, 1H), 7.96 (d, j=7.23 Hz, 1H), 8.05 (s, 1H), 8.18 (d, j=7.11 Hz, 1H), 8.66 (s, 1H), 9.16 (t, j=5.73 Hz, 1H); MS (DCI) m/e 375 (MH$^+$).

Anal. Calcd. for $C_{23}H_{26}N_4O$/2.8 HCl/0.4 H$_2$O: C, 56.92; H, 6.55; N, 11.54.

Found: C, 57.10; H, 6.17; N, 11.58.

Example 28—3,6-dihydro-4-(1-naphthalenyl)-N-(5-ethoxy-4-pyrimidinyl)- 1-(2H)-pyridinepropanamine fumarate In a similar manner 3,6-dihydro-4-(1-naphthalenyl)-N-(5-ethoxy-4-pyrimidinyl)- 1-2H)-pyridinepropanamine was prepared from 3,6-dihydro- 4-(1-naphthalenyl)-1(2H)-pyridinepropanamine by reaction with 4-chloro- 5-ethoxypyrimidine.

mp 115°–117° C.: 58% yield; IR (KBr) 1704, 1644, 1596, 1372, 1268, 1206, 1176 cm$^{-1}$; $^1$H NMR (DMSO-d$_6$) δ 1.34 (t, j=6.93 Hz, 3H), 1.93 (m, 2H), 2.58 (br s, 2H), 2.88 (t, j=7.13 Hz, 2H), 3.11 (t, j=5.57 Hz, 2H), 3.46 (m, 2H), 3.53 (br s, 2H), 4.07 (q, j=6.97 Hz, 2H), 5.71 (br s, 1H) 7.06 (t, j=5.78 Hz, 1H), 7.29 (d, j=6.91 Hz, 1H), 7.44–7.53 (m, 3H), 7.76 (s, 1H), 7.84 (d, j=8.17 Hz, 1H) 7.90–8.01 (m, 2H), 8.10 (s, 1H); MS (DCI) m/e 389 (MH$^+$).

Anal. Calcd. for $C_{24}H_{28}N_4O$/2.6 $C_4H_4O_4$/0.6 $C_2H_6O$: C, 59.56; H, 5.90; N, 7.80.

Found: C, 59.41;H, 6.23; N, 7.41.

Example 29—3,6-dihydro:4-(1-naphthalenyl)-N-(3-methoxy-4-pyridinyl)- 1(2H)-pyridinepropanamine fumarate In a similar manner, compound 3,6-dihydro-4-(1-naphthalenyl)-N-( 3-methoxy-4-pyridinyl)-1(2H)-pyridinepropanamine was prepared from 3,6-dihydro-4-(1-naphthalenyl)-1(2H)-pyridinepropanamine by reaction with 4-bromo-3-methoxypyridine employing N-methylmorpholine as solvent.

mp 123°–125° C.: 50% yield; IR (Kbr) 3402, 3050, 2942, 2774, 2552, 1940, 1462, 1072, 1014, 978, 922, 822, 740, 690, 634, 594, 568, cm$^{-1}$; $^1$H NMR (DMSO d$_6$) δ 1.89 (t, j=6.90 Hz, 2H), 2.49 (s, 2H), 2.54 (bs, 2H), 2.75 (bt, j=9.0 Hz, 2H), 2.93 (t, j=5 Hz, 2H), 3.36 (bs, 4H), 3.86 (s, 3H), 5.72 (s, 1H), 6.57 (s, 4H), 6.81 (d, j=6 Hz, 1H), 7.32 (d, j=6.90 Hz, 2H). 7.51–7.45 (m, 3H), 7.85 (d, j=8.10 Hz, 1H), 8.02–7.90 (m, 4H); MS (DCI) m/e 374 (MH$^+$).

Anal. calcd. for $C_{24}H_{27}N_3O_1$/2.7 $C_4H_4O_4$: C, 60.85; H,5.55; N, 6.12.

Found: C, 60.52; H, 5.44; N, 6.06.

Example 30—3,6-dihydro-4-(1-naphthalenyl)-N-(3-chloro-2-pyrazinyl)- 1(2H)-pyridinepropanamine fumarate In a similar manner, compound 3,6-dihydro-4-(1-naphthalenyl)-N-( 3-chloro-2-pyrazinyl)-1(2H)-pyridinepropanamine was prepared from 3,6-dihydro-4-(1-naphthalenyl)-1(2H)-pyridinepropanamine by reaction with 2,3-dichloropyrazine.

mp 189° C.: 75% yield; IR (Kbr) 3360, 3046, 2974, 2920, 2402, 1978, 1708, 1654, 1452, 1432, 1068, 942, 928, 854, 840, 704, cm$^{-1}$; $^1$H NMR (DMSO d$_6$) δ 1.93 (t, j=6.60 Hz, 2H), 2.49 (bs, 1H), 2.55 (bs, 2H), 2.80 (t, j=6.9 Hz, 2H), 2.98 (t, j=5.7, 2H), 3.44 (bs, 2H), 3.48 (d, j=6 Hz, 2H), 5.71 (s, 1H), 6.58 (s, 2H), 7.27 (d, j=1.20 Hz, 1H), 7.54–7.44 (m, 5H), 7.85 (d, j=8.10 Hz, 1H), 8.03–7.90 (m., 4H); MS (DCI) m/e 379 (MH$^+$).

Anal. calcd. for $C_{22}H_{23}N_4Cl_1$/1.0 $C_4H_4O_4$: C, 63.09; H, 5.50; N, 11.32.

Found: C, 62.97; H, 5.44; N, 11.26.

Example 31—3,6-dihydro-4-(1-naphthalenyl)-N-(3-methoxy-2-pyrazinyl)- 1(2H)-pyridinepropanamine fumarate A mixture of N-[3-(1,2,5,6-tetrahydro-4-naphthalen-1-ylpyridin-1-yl)prop-1-yl]-3-chloro-2-pyrazineamine (0.47 g, 1.24 mmol), sodium methoxide (0.34 g, 6.21 mmol) and copper (I) iodide in 20 mL of MeOH was placed in a bomb and heated at 100° C. for 24 h. The reaction was cooled to R.T., filtered through celite, extracted with 3 portions of 20 mL of CH$_2$Cl$_2$ and washed with 20 mL of sat. aqueous NaHCO$_3$. The combined organic phases were dried with Na$_2$SO$_4$, filtered, and evaporated in vacuo. Silica gel chromatography (100:0:0 to 95:5:0.5 CH$_2$Cl$_2$:MeOH:N H$_4$OH gradient) of the concentrate gave 0.35 g (0.92 mmol, 74%) of the free base. To a solution of the free base (0.35 g, 0.92 mmol) in 5 mL of EtOAc was added fumaric acid (0.21 g, 1.84 mmol) in 3 mL of MeOH. The fumarate salt was recrystallized in EtOAc/EtOH to yield 0.37 g (0.76 mmol, 82%) of the title compound as a white crystalline powder after drying in vacuo at 0.1 mmHg for 24 h, mp 175° C.: IR (Kbr) 3370, 3062, 2944, 2406, 1930, 1650, 1076, 1054, 1004, 980, 924, 802,790, 758, 590, cm$^{-1}$; $^1$H NMR (DMSO d$_6$) δ 1.93 (t, j=6.60 Hz, 2H), 2.51 (s, 1H), 2.57 (bs, 2H), 2.80 (t, j=6.90 Hz, 2H), 3.01 (t, j=6.60 Hz, 2H), 3.44 (bs, 4H), 3.88 (s, 3H), 5.74 (s, 1H), 6.61 (bs, 2H), 6.93 (bs, 1H), 7.24 (d, j=3.30 Hz, 1H), 7.34 (d, j=6.90 Hz, 1H), 7.55–7.47 (m, 4H), 8.03–7.84 (m, 3H); MS (DCI) m/e 375 (MH$^+$).

Anal. calcd. for $C_{23}H_{26}N_4O_1$/1.0 $C_4H_4O_4$: C, 66.11; H, 6.16; N, 11.42.

Found: C, 65.83; H, 6.24; N, 11.33.

Example 32—3,6-dihydro-N-(5-methoxy-4-pyrimidinyl)-4-(1-naphthalenyl)- 1(2H)-pyridinebutanamine fumarate 3,6-Dihydro-4-(1-naphthalenyl)-1-(2H)-pyridinebutanamine (500 mg, 1.78 mmol), 4-chloro-5-methoxypyrimidine (344 mg, 2.67 mmol), and N,N-diisopropylethylamine (0.93 mL, 5.35 mmol) were dissolved in acetonitrile (30 mL). The solution was placed in a Parr bomb and heated at 110° C. for 48 h. Upon cooling to room temperature the crude mixture was concentrated, diluted with chloroform (200 mL) and washed with 50 mL portions of aqueous 10% potassium carbonate and saturated aqueous sodium chloride. The organic layer was dried over anhydrous magnesium sulfate, filtered, and concentrated. Silica gel chromatograpy (97.5:2.5:0.25 $CH_2Cl_2$: $MeOH:NH_4OH$) of the concentrate gave the title compound (552 mg, 79%). The fumarate salt was made by dissolving the free base (552 mg, 1.42 mmol) along with fumaric acid (330 mg, 2.84 mmol) in a solution of hot EtOAc (20 mL) followed by the addition of minimal amounts of MeOH. Upon cooling to room temperature overnight the resultant crystals (497 mg, 58%) were collected by filtration and dried at 65° C. under vacuum (0.05 mm Hg) for 20 h, mp 124°–125° C.: M.S. (DCI); m/e 389 ($MH^+$); I.R. (KBr); 775, 1040, 1260, 1640; $^1H$ NMR (MeOD): δ 2.25 (m, 2H), 2.69 (br d, 1H), 2.86 (br m, 1H), 3.16 (s ,3H), 3.36 (t, J=8.43 Hz, 2H), 3.48 (m, 2H), 3.79 (t, J=7.22 Hz, 2H), 3.88 (m, 1H), 3.91 (s, 3H), 4.10 (br d, 1H), 5.78, (br s, 1H), 6.97 (t, J=7.95, 1H), 7.35 (d, J=7.01, 1H), 7.44–7.54 (m, 5H), 7.85–7.96 (m, 3H).

Anal. Calc'd. for $C_{24}H_{28}N_4O_1/1.7C_4H_4O_4/0.3C_2H_6O_1$: C, 62.89; H,6.15; N, 9.34.

Found: C, 62.96; H, 6.50; N, 9.11.

Example 33—3,6-dihydro-N-(3-methoxy-2-pyridinyl)-4-(1-naphthalenyl)- 1(2H)pyridinepropanamine fumarate 3,6-Dihydro-4-(1-naphthalenyl)-1-(2H)-pyridinepropanamine (312 mg, 1.17 mmol), 2-bromo-3-methoxypyridine (264 mg, 1.41 mmol), and 4-methylmorpholine (0.75 mL) were heated in a Parr bomb at 140° C. for 18 h. The crude mixture upon cooling was diluted with chloroform (200 mL) and washed with 50 mL portions of agueous 10% potassium carbonate and saturated aqueous sodium chloride. The organic layer was dried over anhydrous magnesium sulfate, filtered, and concentrated. Silica gel chromatography (97.5:2.5:0.25 $CH_2Cl_2:MeOH:NH_4OH$) of the concentrate gave the title compound ( 92 mg, 21%). The fumarate salt was made by dissolving the free base (92 mg, 0.25 mmol) along with fumaric acid (57 mg, 0.49 mmol) in a solution of hot EtOAc (10 mL) followed by the addition of minimal amounts of MeOH. Upon cooling to room temperature overnight the resultant crystals (64 mg, 41%) were collected by filtration and dried at 65° C. under vacuum (0.05 mm Hg) for 20 h, mp 90° C. (d); M.S. (DCI); m/e 374 ($MH^+$); I.R. (KBr); 770, 1050, 1250, 1290,1710, 2100–3700; $^1H$ NMR (DMSO-d6): δ 1.87 (m, 2H), 2.54 (br s, 2H), 2.75 (br s, 2H), 2.96 (br s, 2H), 3.39 (br s, 4H), 3.74 (s, 3H), 5.72 (br s, 1H), 6.45 (m, 1H), 6.95 (d, J=7.69 Hz, 1H), 7.31 (d, J=6.14 Hz, 1H), 7.44–7.58 (m, 4H), 7.83 (d, J=9.16 Hz, 1H), 7.91–7.97 (m, 2H).

Anal. Calc'd. for $C_{24}H_{27}N_3O_1/2.2C_4H_4O_4$: C, 62.65; H, 5.74; N, 6.68.

Found: C, 62.46; H, 5.98; N, 6.74.

Example 34—3,6-dihydro-N-(3-ethoxy-2-pyridinyl)-4-(1-naphthalenyl)- 1(2H)-pyridinepropanamine fumarate In an similar manner 3,6-dihydro-N-(3-ethoxy-2-pyridinyl)-4-(1-naphthalenyl)- 1(2H)-pyridinepropanamine was prepared by reacting 3,6-dihydro-4-(1-naphthalenyl)-1(2H)-pyridinepropanamine with 2-bromo- 3-ethoxypyridine in diisopropylethylamine as solvent.

mp 95° C. (dec): 2% yield; M.S. (DCI); m/e 388 ($MH^+$).

Anal. Calc'd. for $C_{25}H_{29}N_3O_1/2.7C_4H_4O_4$: C, 61.35; H, 5.72; N, 5.99.

Found: C, 61.21; H, 5.80; N, 6.03.

Example 35—3,6-dihydro-N-(6-trifluoromethyl-2-pyridinyl)-4-(1-napthalenyl)- 1(2H)-pyridinepropanamine fumarate 3,6-Dihydro-4-(1-naphthalenyl)-1(2H)-pyridinepropanamine (500 mg, 1.88 mmol), 2-chloro-6-trifluoromethylpyridine (511 mg, 2.82 mmol), and N,N-diisopropylethylamine (726 mg, 5.63 mmol) were dissolved in acetonitrile (30 mL). The solution was placed in a Parr bomb and heated at 110° C. for 48 h. Upon cooling to room temperature the crude mixture was concentrated, diluted with chloroform (200 mL) and washed with 50 mL portions of aqueous 10% potassium carbonate and saturated aqueous sodium chloride. The organic layer was dried over anhydrous magnesium sulfate, filtered, and concentrated. Silica gel chromatograpy (97.5:2.5:0.25 $CH_2Cl_2:MeOH:NH_4OH$) of the concentrate gave the title compound (78 mg, 11%). The fumarate salt was made by dissolving the free base (78 mg, 0.19 mmol) along with fumaric acid (45 mg, 0.39 mmol) in a solution of hot EtOAc (10 mL) followed by the addition of minimal amounts of MeOH. Upon cooling to room temperature overnight the resultant crystals (58 mg, 52%) were collected by filtration and dried at 65° C. under vacuum (0.05 mm Hg) for 20 h, mp 144°–146° C.: M.S. (DCI); m/e 412 ($MH^+$); I.R. (KBr); 770, 800, 1130, 1170, 1290, 2100– 3600; $^1H$ NMR (DMSO): δ 1.86 (m, 2H), 2.50 (m, 2H), 2.75 (t, J=7.54 Hz, 2H), 2.94 (t, J=5.58 Hz, 2H), 3.36 (m, 4H), 5.70, (br s, 1H), 6.72 (d, J= 8.53 Hz, 1H), 6.87 (d, J=7.15 Hz, 1H), 7.20 (br s, 1H), 7.29 (t, J=7.11 Hz, 1H), 7.44–7.58 (m, 4H), 7.83 (d, J=8.19 Hz, 1H), 7.90–7.99 (m, 3H).

Anal. Calc'd. for $C_{24}H_{24}N_3F_3/1.5C_4H_4O_4$: C, 61.53; H, 5.16; N, 7.18. a Found: C, 61.38; H, 5.26; N, 7.18.

Example 36—3,6-dihydro-N-(5-chloro-2-pyridinyl)-4-(1-naphthalenyl)- 1(2H)-pyridinepropanamine fumarate In a similar fashion 3,6-dihydro-N-(5-chloro-2-pyridinyl)-4-(1- naphthalenyl)-1(2H)-pyridinepropanamine was synthesized by reacting 2,5-dichloropyridine with 4-(1-naphthalenyl)-1(2H)-pyridinepropanamine.

mp 159°–161° C.: 53% yield; M.S. (DCI); m/e 378 ($MH^+$); I.R. (KBr); 770, 800, 1395, 1490, 1590, 1710; $^1H$ NMR (DMSO-d6): δ 1.81 (m, 2H), 2.48 (br m, 2H), 2.66 (t, J=7.39 Hz, 2H), 2.87 (t, J=5.61 Hz, 2H), 3.28 (br m, 4H), 5.71 (br s, 1H), 6.44 (dd, J=16.88, 7.26 Hz, 2H), 7.04 (br s, 1H), 7.29–7.52 (m, 5H), 7.82 (d, J=8.21 Hz, 1H),7.89–7.98 (m, 2H).

Anal. Calc'd. for $C_{23}H_{24}N_3Cl_1/1.1C_4H_4O_4$: C, 65.09; H, 5.66; N, 8.31.

Found: C, 65.22; H, 5.72; N, 8.49.

Example 37—3,6dihydro-N-(4-trifluromethyl-2-pyridinyl)-4-(1-napthalenyl-1(2H)-pyridinepropanamine fumarate In a similar fashion 3,6-dihydro-N-(4-trifiuromethyl-2-pyridinyl)-4-( 1-naphthalenyl)-1(2H)-pyridinepropanamine was synthesized from 2-chloro- 4-trifluoromethylpyridine and 4-(1-naphthalenyl)-1(2H)-pyridinepropanamine.

mp 148°–152° C.: 45% yield; M.S. (DCI); m/e 412 ($MH^+$); I.R. (KBr); 770, 980, 1180, 1300, 1570, 1710; $^1H$ NMR (DMSO-$d_6$): δ 1.91 (m, 2H), 2.55 (br s, 2H), 2.83 (t, J=7.68 Hz, 2H), 3.03 (t, J=5.60 Hz, 2H), 3.38 (br s, 2H), 3.45 (br s, 2H), 5.71 (br s, 1H), 6.69 (d, J=5.36 Hz, 1H), 6.75 (s, 1H), 7.20 (br s, 1H), 7.29 (d, J=6.99 Hz, 1 H), 7.44–7.52 (m, 3H), 7.83 (d, J=8.21 Hz, 1H), 7.89–8.00 (m, 2H), 8.19 (d, J=5.26 Hz).

Anal. Calc'd. for $C_{24}H_{24}N_3F_1/1.9C_4H_4O_4$: C, 65.05; H, 5.04; N, 6.65.

Found: C, 64.38; H, 5.32; N, 7.78.

Example 38—4-(1-naphthalenyl)-N-(5-methoxy-4-pyrimidinyl)-1-piperidinepropanamine fumarate 4-(1-Naphthalenyl)-1-piperidinepropanamine (0.76 g, 2.8 mmol), and 4-chloro-5-methoxypyrimidine (0.45 g, 3.1 mmol) were dissolved in acetonitrile (80 mL) and micropulverized potassium carbonate (1.0 g) was added. The mixture was refluxed for 24 h, the solvent removed in vacuo, and the residue extracted using $CH_2Cl_2$/brine. The $CH_2Cl_2$ layer was washed with water, dried over $Na_2SO_4$, filtered, and concentrated in vacuo. Silica gel chromatography ($CH_2Cl_2$ folowed by 95:5:0.5 to 90:10:1 $CH_2Cl_2$:MeOH:$NH_4OH$ gradient) gave the free base (540 mg, 51%). The purified material was dissolved in EtOAc and treated with 2.0 eq. of fumaric acid in MeOH. Triple recrystallization from EtOH/EtOAc gave the title compound as an off-white crystalline solid (220 mg, 22%), mp 138°–140° C.: IR (KBr) 1704, 1642, 1600, 1368, 1316, 1274 cm$^{-1}$; $^1$H NMR (DMSO-d$_6$) δ 1.65 (br, 1H), 1.90 (br, 6H), 2.69 (br, 1H), 2.87 (br m, 4H), 3.42 (m, 2H), 3.55 (m, 1H), 3.82 (s, 3H), 7.27–7.58 (m, 5H), 7.75–7.80 (m, 2H), 7.91 (d, j=7.6 Hz, 1H), 8.10 (br s, 1H), 8.16 (d, j=8.1 Hz, 1H); MS (DCI) m/e 377 (MH$^+$).

Anal. Calcd. for $C_{23}H_{28}N_4O/2.6\ C_4H_4O_4/0.3\ C_2H_6O$: C, 59.00; H, 5.85; N, 8.09.

Found: C, 58.97; H, 6.20; N, 7.83.

Example 39—3,6-dihydro-N-(1-naphthalenyl)-4-(1-naphthalenyl)-1(2H)-pyridinepropanamine fumarate 3,6-Dihydro-4-(1-naphthalenyl)-1(2H)-pyridinepropanol (VI: 500 mg, 1.87 mmol) was dissolved in methylene chloride (20 mL) followed by the addition of triethylamine (0.39 mL, 2.81 mmol) and cooled to 0° C. Methanesulfonyl chloride (0.17 mL, 2.24 mmol) was added dropwise and reaction was allowed to stir for 30 min while warming to room temperature. Solvent was then removed in vacuo yielding IV as a crude solid. This material was then dissolved in acetonitrile (5 mL) followed by the addition of 1-aminonaphthalene (V: 1.34 g, 9.35 mmol) and N,N-diisopropylethylamine (1.63 mL, 9.35 mmol). After heating at 110° C. for 24 hours in a Parr bomb, the reaction was cooled to room temperature and diluted with chloroform (700 mL) and washed with 200 mL portions of aqueous 10% potassium carbonate and saturated aqueous sodium chloride. The organic layer was dried over anhydrous magnesium sulfate, filtered, and concentrated. Silica gel chromatography (97.5:2.5:0.25 $CH_2Cl_2$:MeOH:$NH_4OH$) of the concentrate gave the title compound (438 mg, 60%). The fumarate salt was made by dissolving the free base (438 mg, 1.12 mmol) along with fumaric acid (259 mg, 2.22 mmol) in a solution of hot EtOAc (30 mL) followed by the addition of minimal amounts of MeOH. Upon cooling to room temperature overnight the resultant crystals (298 mg, 51%) were collected by filtration and dried at 65° C. under vacuum (0.05 mm Hg) for 20 h, mp 166°–167° C.: M.S. (DCI); m/e 393 (MH$^+$); I.R. (KBr); 775, 970, 1280, 1540, 1710, 3400; $^1$H NMR (DMSO-d6): δ 2.16 (m, 2H), 3.38 (m, 5H), 5.63 (br s, 1H), 6.71 (d, J=7.63 Hz, 1H), 7.15–7.43 (m, 7H), 7.77–7.96 (m, 5H).

Anal. Calc'd. for $C_{28}H_{28}N_2/1.1C_4H_4O_4$: C, 74.81; H, 6.28; N, 5.38.

Found: C, 75.15; H, 6.09; N, 5.43.

Example 40—3,6-dihydro-N-(2-methoxyphenyl)-4-(1-naphthalenyl)- 1-(2H)-pyridinepropanamine fumarate In a similar fashion 3,6-dihydro-N-(2-methoxyphenyl)-4-(1-naphthalenyl)- 1(2H)-pyridinepropanamine (324 mg, 46%) was synthesized from 2-methoxyaniline and 3,6-dihydro-4-(1-naphthalenyl)- 1(2H)-pyridinepropanol. The fumarate salt was made by dissolving the free base (324 mg, 0.87 mmol) along with fumaric acid (202 mg, 1.74 mmol) in a solution of hot EtOAc (10 mL) followed by the addition of minimal amounts of MeOH. Upon cooling to room temperature overnight the resultant crystals (229 mg, 54%) were collected by filtration and dried at 65° C. under vacuum (0.05 mm Hg) for 20 h, mp 169°–170 ° C.: M.S. (DCI); m/e 373 (MH$^+$); I.R. (KBr); 775, 1025, 1250, 1600, 1690, 3360; $^1$H NMR (DMSO-d6): δ 2.15 (m, 2H), 2.79 (br s, 2H), 3.30 (m, 4H), 3.55 (t, J=6.03 Hz, 2H), 3.83 (s, 3H), 3.93 (m, 2H), 5.77 (t, J=1.63 1H), 6.63– 6.72 (m, 2H), 6.68–6.86 (m, 2H), 7.30 (d, J=7.04 Hz, 1H), 7.42–7.49 (m, 3H), 7.79–7.97 (m, 3H).

Anal. Calc'd. for $C_{25}H_{28}N_2O_1/1.0C_4H_4O_4$: C, 71.29 H, 6.60 N, 5.73.

Found: C, 70.90; H, 6.24; N, 5.67.

Example 41—3,6-dihydro-N-(3-chlorophenyl)-4-(1-naphthalenyl)-1(2H)-pyridinepropanamine fumarate In a similar fashion 3,6-dihydro-N-(3-chlorophenyl)-4-(1-naphthalenyl)- 1(2H)-pyridinepropanamine (235 mg, 33%) was synthesized from 2-methoxyaniline and 3,6-dihydro-4-(1-naphthalenyl)- 1(2H)-pyridinepropanol. The fumarate salt was made by dissolving the free base (235 mg, 0.62 mmol) along with fumaric acid (145 mg, 1.25 mmol) in a solution of hot EtOAc (10 mL) followed by the addition of minimal amounts of MeOH. Upon cooling to room temperature overnight the resultant crystals (194 mg, 63%) were collected by filtration and dried at 65° C. under vacuum (0.05 mm Hg) for 20 h, mp 172°–173° C.: M.S. (DCI); m/e 377 (MH$^+$); I.R. (KBr); 760, 790, 1310, 1580, 1690, 3180; $^1$H NMR (DMSO-d6): δ 2.12 (m, 2H), 2.80 (br s, 2H), 3.30 (m, 4H), 3.53 (t, J=5.99 Hz, 2H), 3.91 (br s, 2H), 5.79 (br s, 1H), 6.56–6.70 (m, 3H), 7.06 (t, J=8.01 Hz, 1H), 7.31 (d, J=6.99 Hz, 1H), 7.42–7.50 (m, 3H), 7.80– 7.89 (m, 2H), 7.97–8.00 (m, 1H).

Anal. Calc'd. for $C_{24}H_{25}N_2Cl_1/1.0C_4H_4O_4$: C, 68.22 H, 5.93 N, 5.68.

Found: C, 68.03; H, 5.61; N, 5.67.

Example 42—3,6-dihydro-N-(3-trifluoromethylphenyl)-4-(1-naphthalenyl)-1(2H)-pyridinepropanamine fumarate In a similar fashion 3,6-dihydro-N-(3-trifluoromethylphenyl)-4-(1-naphthalenyl)-1(2H)-pyridinepropanamine (275 mg, 36%) was synthesized from 2-trifluoromethylaniline and 3,6-dihydro-4-(1-naphthalenyl)- 1(2H)-pyridinepropanol. The fumarate salt was made by dissolving the free base (275 mg, 0.67 mmol) along with fumaric acid (156 mg, 1.34 mmol) in a solution of hot EtOAc (10 mL) followed by the addition of minimal amounts of MeOH. Upon cooling to room temperature overnight the resultant crystals (48 mg, 14%) were collected by filtration and dried at 65° C. under vacuum (0.05 mm Hg) for 20 h, mp 169°–170 ° C.: M.S. (DCI); m/e 411 (MH$^+$); I.R. (KBr); 700, 780, 1120, 1160, 1350, 1580; $^1$H NMR (DMSO-d$_6$): δ 1.84 (m, 2H), 2.48 (br s, 2H), 2.69 (t, J=7.29 Hz, 2H), 2.87 (t, J=5.74 Hz, 2H), 3.14 (t, J=6.71 Hz, 2H), 3.28 (m, 2H), 5.71 (br s, 1H), 6.80 (m, 3H), 7.28 (m, 2H), 7.48 (m, 3H), 7.82 (d, j=8.19 Hz, 1H), 7.89–7.98 (m, 2H).

Anal. Calc'd. for $C_{25}H_{25}N_2F_3/1.0C_4H_4O_4$: C, 66.15 H, 5.55 N, 5.32.

Found: C, 65.88; H, 5.39; N, 5.28.

A number of Formula (I) compounds and their potency in inhibiting 5-HT uptake are tabulated in Table 1.

TABLE 1

Inhibition of Serotonin Reuptake by Formula (I) Compounds

| Example | SUI‡ |
|---|---|
| 14 | ** |
| 15 | ** |
| 16 | ** |
| 17 | *** |
| 18 | ** |
| 19 | ** |
| 20 | *** |
| 21 | *** |
| 22 | *** |
| 23 | ** |
| 24 | * |
| 25 | * |
| 26 | ** |
| 27 | *** |
| 28 | *** |
| 29 | ** |
| 30 | *** |
| 31 | *** |
| 32 | ** |
| 33 | *** |
| 34 | *** |
| 35 | ** |
| 36 | *** |
| 37 | ** |
| 38 | *** |
| 39 | *** |
| 40 | *** |
| 41 | ** |
| 42 | ** |

‡SUI designates Serotonin Uptake Inhibition potency for selected representative compounds of Formula (I). In vitro $IC_{50}$ values (nM of test compound that inhibits uptake by 50%) are indicated as follows:
* = below 500 nM
** = below 100 nM
*** = below 10 nM

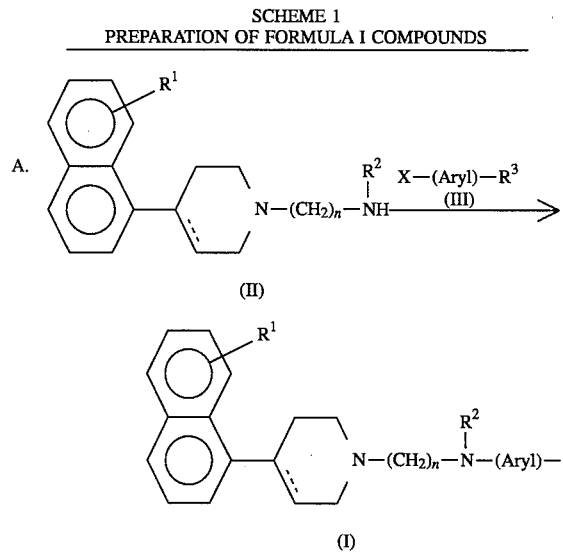

SCHEME 1
PREPARATION OF FORMULA I COMPOUNDS

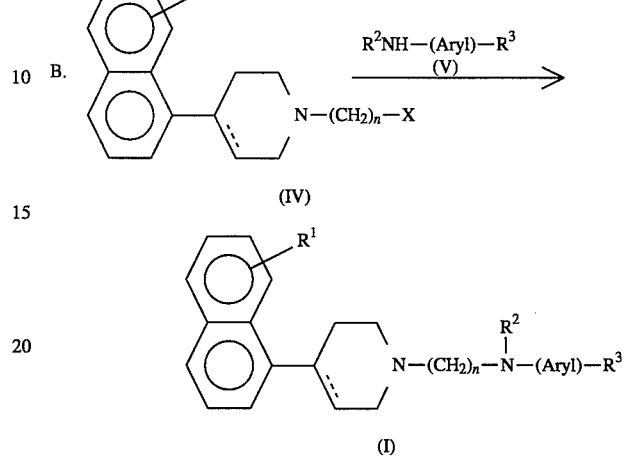

SCHEME 2
PREPARATION OF INTERMEDIATE COMPOUNDS

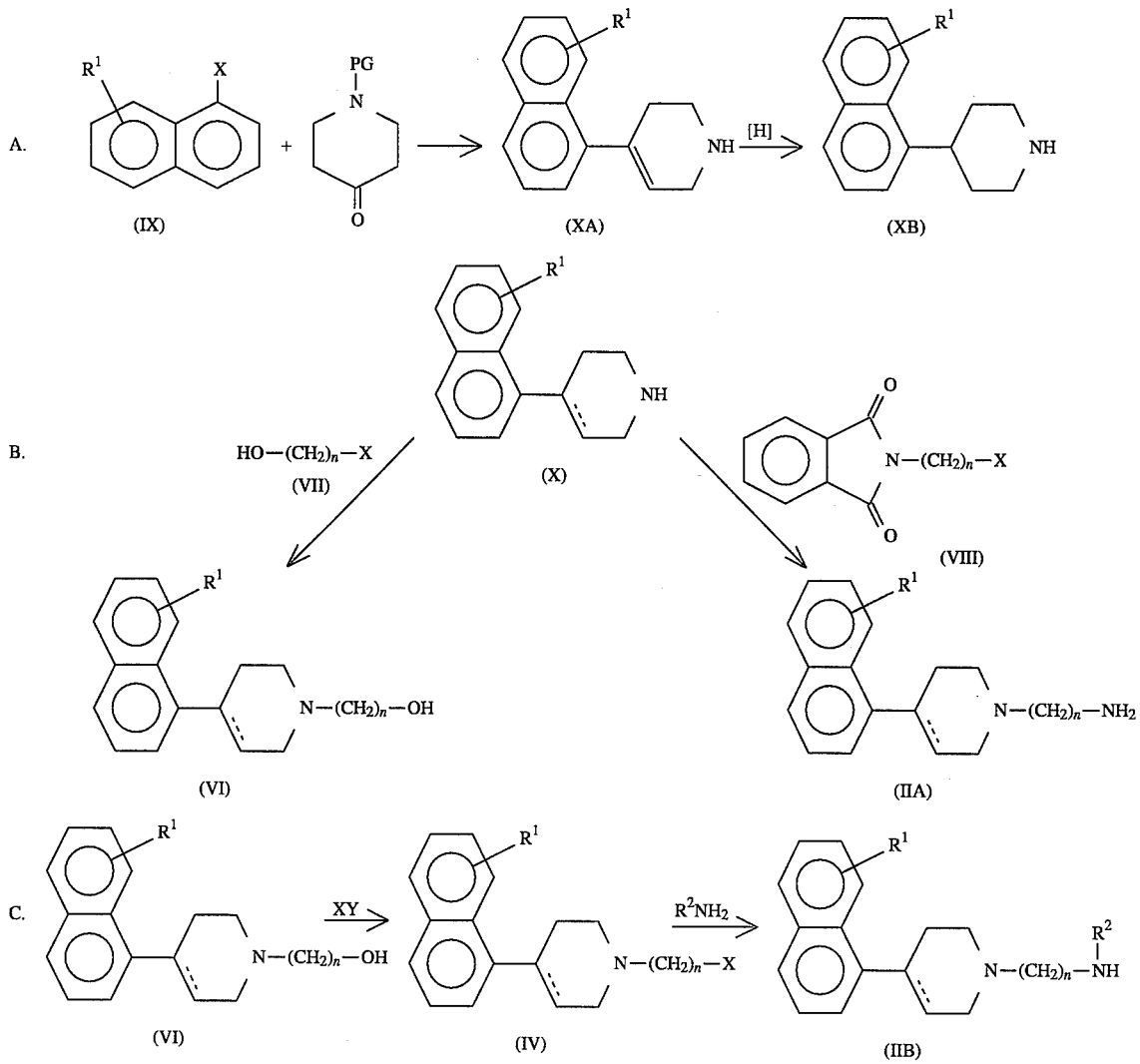

We claim:

1. A compound of Formula (I) or a pharmaceutically acceptable

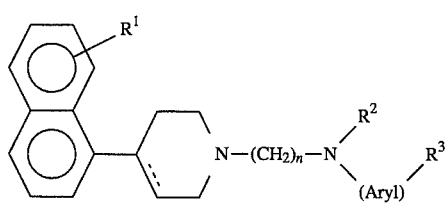

acid addition salt thereof wherein

R$^1$ is hydrogen, lower alkyl, lower alkoxy, and halogen;

R$^2$ is hydrogen and lower alkyl;

R$^3$ is hydrogen, lower alkyl, lower alkoxy, halogen, and trifluoromethyl;

the symbol n is an integer from 2 to 4;

the dotted and solid lines denote either a single or a double covalent bond; and (Aryl) is selected from phenyl, naphthyl, pyridine, pyrimidine, and pyrazine.

2. A compound of claim 1 wherein n is 3.

3. A compound of claim 1 wherein (Aryl) is phenyl and naphthyl.

4. A compound of claim 1 wherein (Aryl) is pyridine, pyrimidine and piperazine.

5. A compound of claim 3 selected from 3,6-dihydro-N-(1-naphthalenyl)-4-(1-naphthalenyl)-1(2H)-pyridinepropanamine fumarate; 3,6-dihydro-N-(2-methoxyphenyl)-4-(1-naphthalenyl)- 1(2H)-pyridinepropanamine fumarate; 3,6-dihydro-N-(3-chlorophenyl)-4-(1-naphthalenyl)-1(2H)-pyridinepropanamine fumarate; and 3,6-dihydro-N-3-trifluoromethylphenyl)-4-(1-naphthalenyl)-1(2H)-pyridinepropanamine fumarate.

6. A compound of claim 4 wherein (Aryl) is pyridine.

7. A compound of claim 4 wherein (Aryl) is pyrimidine.

8. A compound of claim 4 wherein (Aryl) is pyrazine.

9. A compound of claim 6 selected from 3,6-dihydro-N-(3-methoxy- 2-pyridinyl)-N-methyl-4-(1-naphthalenyl)-1(2H)-pyridinepropanamine fumarate; 3,6-dihydro-N-(3-ethoxy-2-pyridinyl)-N-methyl-4-(1-naphthalenyl)- 1(2H)- pyridinepropanamine fumarate; 3,6-dihydro-N-methyl-N-(4-trifluoromethyl-2-pyridinyl)-4-(1-naphthalenyl)-1(2H)-pyridinepropanamine fumarate; 3,6-dihydro-N-methyl-N-(5-chloro-2-pyridinyl)- 4-(1-naphthalenyl)-1(2H)-pyridinepropanamine fumarate; 3,6-dihydro-N-methyl-N-(6-trifluoromethyl-2-pyridinyl)-4-(1-naphthalenyl)- 1(2H)-pyridinepropanamine fumarate; 3,6-dihydro-N-methyl-N-(4-chloro- 2-pyridinyl)-4-(1-naphthalenyl)-1(2H)-pyridinepropanamine; 3,6-dihydro-N-methyl-N-( 2-chloro-4-pyridinyl)-4-(1-naphthalenyl)-1(2H)-pyridinepropanamine fumarate; 3,6-dihydro-N-(3-methoxy-2-pyridinyl)- 4-(1-naphthalenyl)-1(2H)-pyridinepropanamine fumarate; 3,6-dihydro-N-( 3-ethoxy-2-pyridinyl)-4-(1-naphthalenyl)-1(2H)-pyridinepropanamine fumarate; 3,6-dihydro-N-(6-trifluoromethyl-2-pyridinyl)-4-(1-naphthalenyl)- 1(2H)-pyridinepropanamine fumarate; 3,6-dihydro-N-(5-chloro-2-pyridinyl)-4-(1-naphthalenyl)-1(2H)-pyridinepropanamine fumarate and 3,6-dihydro-N-(4-trifluromethyl-2-pyridinyl)-4-(1-naphthaleny)- 1(2H)-pyridinepropanamine fumarate.

10. A compound of claim 7 selected from 3,6-dihydro-N-(5-methoxy- 4-pyrimidinyl)-N-methyl-4-(1-naphthalenyl)1(2H)-pyridinepropanamine fumarate; 3,6-dihydro-N-(5-methoxy-4-pyrimidinyl)-N-ethyl-4-(1-napthalenyl)- 1(2H)-pyridinepropanamine fumarate; 3,6-dihydro-4-(7-methoxy-1-naphthalenyl)-N-(5-methoxy-4-pyrimidinyl)-1( 2H)-pyridinepropanamine fumarate; 3,6-dihydro-4-(7-fluoro- 1-naphthalenyl)-N-( 5-methoxy-4-pyrimidinyl)-1(2H)-pyridinepropanamine fumarate; 3,6-dihydro- 4-(7-chloro-1-naphthalenyl)-N-(5-methoxy-4-pyrimidinyl)-1(2H)-pyridinepropanamine fumarate; 4-(1-naphthalenyl)-N-(5-methoxy-4-pyrimidinyl)-1-piperidinepropanamine fumarate; 3,6-dihydro-4-(1-naphthalenyl)-N-( 5-methoxy-4-pyrimidinyl)-1(2H)-pyridineethanamine fumarate; 3,6-dihydro-4-(1-naphthalenyl)-N-(5-methoxy-4-pyrimidinyl)- 1(2H)-pyridinepropanamine hydrochloride; 3,6-dihydro-4-(1-naphthalenyl)-N-( 5-ethoxy-4-pyrimidinyl)-1(2H)-pyridinepropanamine fumarate and 3,6-dihydro-N-(5-methoxy-4-pyrimidinyl)-4-(1-naphthalenyl)- 1(2H)-pyridinebutanamine fumarate.

11. A compound of claim 8 selected from 3,6-dihydro-4-( 1-naphthalenyl)-N-( 3-chloro-2-pyrazinyl)-1(2H)-pyridinepropanamine fumarate and 3,6-dihydro-4-(1-naphthalenyl)-N-(3-methoxy-2-pyrazinyl)- 1(2H)-pyridinepropanamine fumarate.

12. A method for ameliorating a state of depression in a mammal comprising administration to the mammal of an effective antidepressant amount of a compound claimed in claim 1.

13. A pharmaceutical composition in unit dosage form suitable for systemic administration to a mammalian host comprising a pharmaceutical carrier and from about 1 to 500 mg of an antidepressant compound selected from the compounds claimed in claim 1.

* * * * *